(12) United States Patent
Luther et al.

(10) Patent No.: US 7,037,294 B2
(45) Date of Patent: May 2, 2006

(54) NEEDLE SAFETY COVER

(75) Inventors: Ronald B. Luther, Newport Beach, CA (US); John I. Muri, Aliso Viejo, CA (US)

(73) Assignee: Luther Research Partners, LLC, Costa Mesa, CA (US)

( * ) Notice: Subject to any disclaimer, the term of this patent is extended or adjusted under 35 U.S.C. 154(b) by 210 days.

(21) Appl. No.: 10/402,106

(22) Filed: Mar. 27, 2003

(65) Prior Publication Data

US 2004/0193116 A1    Sep. 30, 2004

(51) Int. Cl.
 *A61M 5/32* (2006.01)
(52) U.S. Cl. ...................... 604/192; 604/110
(58) Field of Classification Search .......... 604/192, 604/198, 263, 110, 163, 164.08
See application file for complete search history.

(56) References Cited

U.S. PATENT DOCUMENTS

| | | | | |
|---|---|---|---|---|
| 2,740,404 A * | 4/1956 | Kohl | ...................... | 604/167.01 |
| 2,847,995 A * | 8/1958 | Adams | ........................ | 604/198 |
| 2,997,043 A * | 8/1961 | Flynn | ......................... | 604/263 |
| 3,354,881 A * | 11/1967 | Bloch | ......................... | 604/198 |
| 3,459,184 A * | 8/1969 | Ring | ...................... | 604/164.08 |
| 3,786,810 A * | 1/1974 | Pannier et al. | ............... | 604/158 |
| 4,887,997 A * | 12/1989 | Okada | ......................... | 604/516 |
| 5,000,167 A * | 3/1991 | Sunderland | .................. | 600/576 |
| 5,163,916 A * | 11/1992 | Sunderland | .................. | 604/198 |
| 5,242,418 A * | 9/1993 | Weinstein | .................... | 604/192 |
| 5,312,359 A * | 5/1994 | Wallace | .................. | 604/164.08 |
| 5,385,556 A * | 1/1995 | Wang et al. | ................. | 604/192 |
| 5,704,917 A * | 1/1998 | Utterberg | .................... | 604/180 |
| 5,891,103 A * | 4/1999 | Burns | ........................ | 604/192 |
| 6,319,232 B1 * | 11/2001 | Kashmer | .................... | 604/192 |
| 2002/0072716 A1 * | 6/2002 | Barrus et al. | ............... | 604/192 |
| 2003/0212373 A1 * | 11/2003 | Hall et al. | ................... | 604/263 |

* cited by examiner

*Primary Examiner*—Sharon Kennedy
(74) *Attorney, Agent, or Firm*—Knobbe, Martens, Olson & Bear LLP

(57) ABSTRACT

A needle safety apparatus comprises a hollow needle having a sharpened distal end and a proximal end. The proximal end is anchored in a syringe barrel adapter. The needle safety apparatus further comprises a protective sheath having a proximal region, a distal region and a slit running between the proximal region and the distal region. The protective sheath is movable between an armed position and a deployed position. When the protective sheath is in the armed position, the hollow needle passes through the slit in the protective sheath distal region. When the protective sheath is in the deployed position, the hollow needle passes through the slit in the protective sheath proximal region.

18 Claims, 5 Drawing Sheets

NEEDLE SAFETY COVER

FIELD OF THE INVENTION

This invention relates generally to needles used in medical treatments, and specifically to a safety cover for use with a hypodermic needle.

BACKGROUND OF THE INVENTION

In the medical field it is often necessary to insert a needle into a patient's body to withdraw materials from, or deliver materials to, the patient's body. After the needle is withdrawn from the patient's body, it will be contaminated with biological fluids. Specifically, an exposed, contaminated needle can easily pierce the skin of medical personnel or other patients, thereby providing a route for spread of disease. The threat of needle prick injuries is especially dangerous in light of diseases that can be transferred through the exchange of bodily fluids, such as hepatitis and the human immunodeficiency virus. An exposed, contaminated needle presents a safety hazard to all people having to handle the needle and its disposal, such as medical personnel and janitorial staff. In addition, if an exposed, contaminated needle contacts other items, such as work surfaces, clothing or other medical instruments, such other items can also be contaminated with biological fluids. Thus, there is a need for a system that reduces the likelihood of contamination between used needles and other objects and/or people.

To address this need, various disposal systems for used needles have been developed. Such systems often require medical personnel to place a used needle in a container specifically adapted to hold used needles. In particular, such containers usually are made from a material that is resistant to puncture by the exposed needle, and usually feature a needle insertion mechanism that prevents inserted needles from later being removed, even if the container is upset or dropped. However, such designs suffer from numerous disadvantages. For example, such containers still require an exposed, contaminated needle to be transported from the patient to the disposal container. In addition, such containers are often large and bulky, and thus consume valuable space in medical facilities. Furthermore, such disposal containers are not useful if a needle must be used in a location where such a disposal container is not present, such as may be necessary in a medical emergency.

SUMMARY OF THE INVENTION

In light of the foregoing, a system that reduces the likelihood of contamination between used needles and other objects and/or people is desired. Preferably, such a system will minimize handling of a needle after removal from the patient's body. Additionally, such a system is preferably easy to use, is inexpensive to manufacture, and will not require specialized disposal apparatuses. In particular, such a system is preferably integral with the needle itself, thus eliminating the need for separate disposal structures. A reduced manufacturing cost allows such devices to be disposable, thus eliminating expenses associated with sterilization.

According to one embodiment of the present invention, a needle safety apparatus comprises a hollow needle having a sharpened distal end and a proximal end. The proximal end is anchored in a syringe barrel adapter. The needle safety apparatus further comprises a protective sheath having a proximal region, a distal region and a slit running between the proximal region and the distal region. The protective sheath is movable between an armed position and a deployed position. When the protective sheath is in the armed position, the hollow needle passes through the slit in the protective sheath distal region. When the protective sheath is in the deployed position, the hollow needle passes through the slit in the protective sheath proximal region.

According to another embodiment of the present invention, an apparatus comprises a hollow needle configured for insertion into a patient's body. The apparatus further comprises a syringe barrel adapter in fluid connection or communication with the hollow needle. The apparatus further comprises a housing assembly supporting the hollow needle and the syringe barrel. The housing assembly has a conduit through which an elongate protective sheath is movably disposed. The elongate protective sheath is movable within the conduit between an armed position wherein a portion of the hollow needle is exposed, and a deployed position wherein the hollow needle is covered by the protective sheath.

According to another embodiment of the present invention, a method comprises inserting an elongate hollow needle into a patient's body. The elongate needle is anchored in a housing assembly having a conduit through which an elongate protective sheath is movably disposed. The method further comprises positioning a distal portion of the elongate protective sheath adjacent to the patient's body. The method further comprises withdrawing the elongate hollow needle from the patient's body while substantially maintaining the distal portion of the elongate protective sheath in a position adjacent to the patient's body.

BRIEF DESCRIPTION OF THE DRAWINGS

Having thus summarized the general nature of the needle safety cover disclosed herein, and its essential features and advantages, certain preferred embodiments and modifications thereof will be apparent to those of ordinary skill in the art from the detailed description herein, which references the following figures.

DETAILED DESCRIPTION OF PREFERRED EMBODIMENTS

As described above, it is desired to have a system that reduces the likelihood of contamination between used needles and other objects and/or people. The various embodiments of the needle safety cover described herein address this desire. In particular, such embodiments provide a needle safety cover that promptly contains a used needle after withdrawal from a patient's body, that is easy to use, that is inexpensive to manufacture, and that is integral with the needle itself, thus eliminating the need to use disposal containers for used needle storage. It is economically feasible to make the various embodiments disclosed herein to be disposable, thus eliminating reuse costs such as sterilization expenses.

Figure 1:
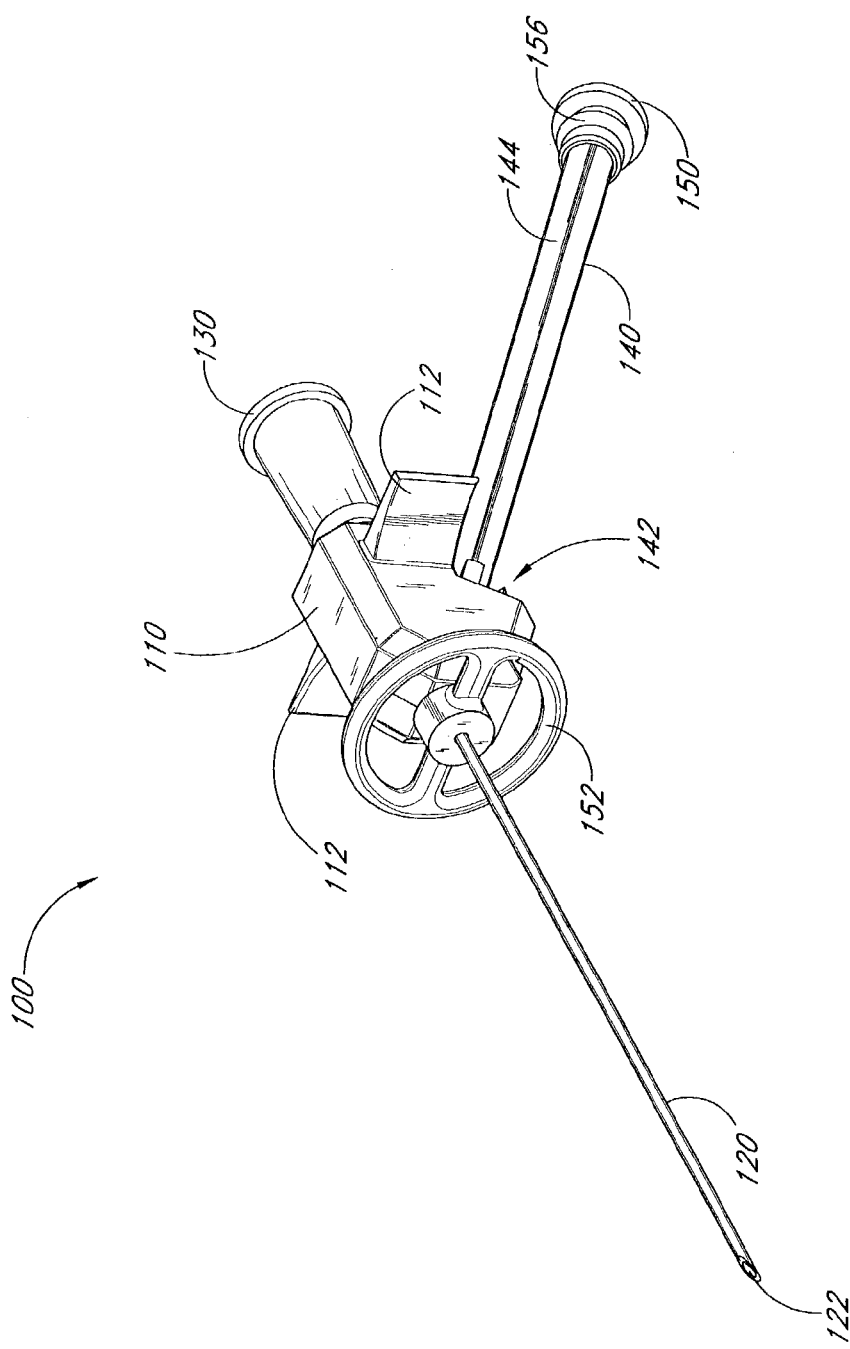
FIG. 1 is a perspective view of a needle safety cover in a ready-for-use, or "armed", configuration.
Figure 2:
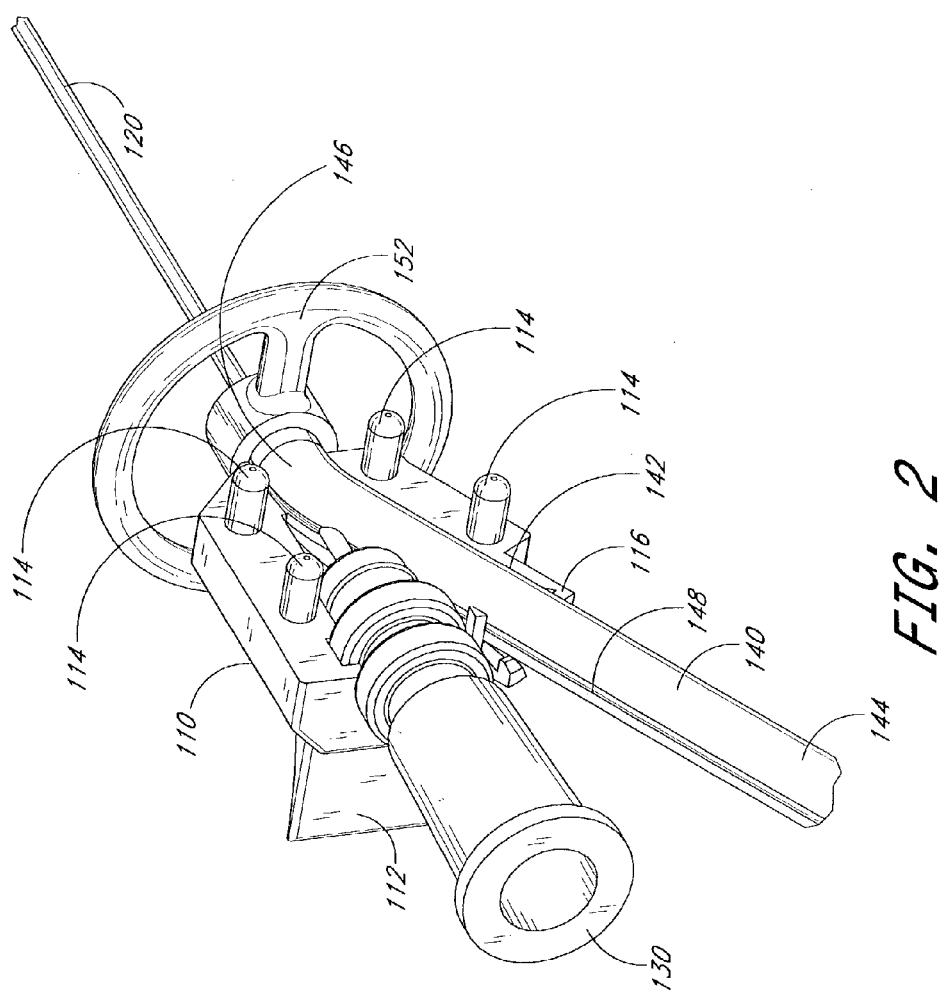
FIG. 2 is a detail partial side cutaway view of the needle safety cover of FIG. 1.
Figure 3:
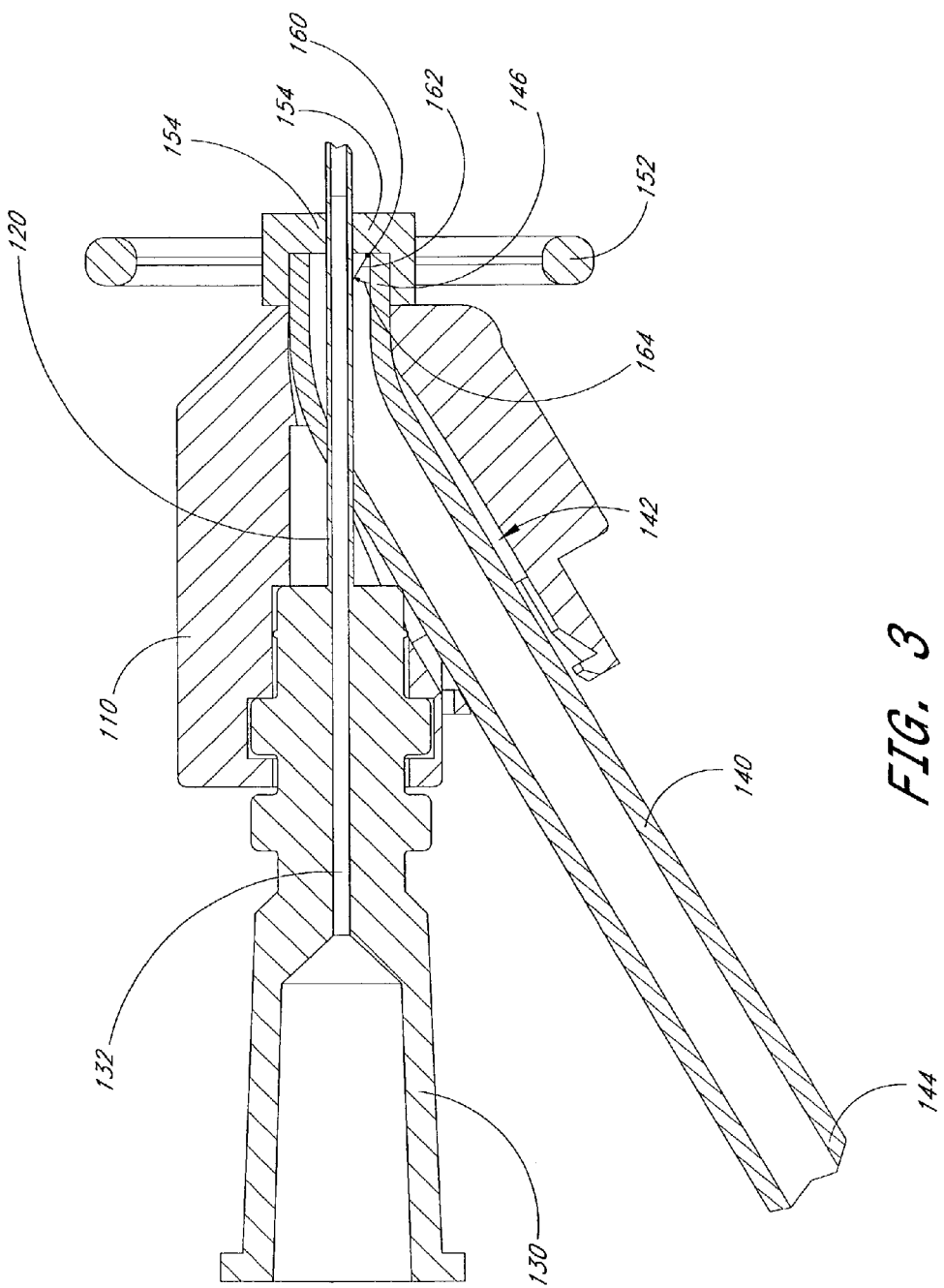
FIG. 3 is a side cutaway view of the needle safety cover of FIG. 1.

FIGS. 1 and 2 illustrate a preferred embodiment of a needle safety cover 100. The needle safety cover 100 comprises a housing assembly 110 that supports a hollow needle 120 and a syringe barrel adapter 130. The housing assembly 110 further comprises a conduit 142 through which a protective sheath 140 is movably disposed. FIG. 3 illustrates the arrangement of these components of the housing assembly 110 in a close-up cutaway view. The housing assembly 110 can be manufactured as two separate side components, one of which is illustrated in FIG. 2, that are secured together (such as, for example, with an epoxy) in an assembly process after the housing assembly interior components have been positioned as desired. In certain embodiments, dowels 114 in one of the side components mate with recessed portions (not shown) in the other side component to aid in properly aligning the two side components during the assembly process.

The housing assembly 110 functions, among other things, to provide the user with an easy-to-hold device that will not slip from the fingers during use. Thus, as illustrated in FIGS. 1 and 2, in certain embodiments the housing assembly further comprises two finger grips 112 disposed on opposite sides of the housing assembly 110 to facilitate handling of the needle safety cover 100. In a preferred embodiment the housing assembly 110 comprises a plastic material, although other appropriate materials can be used in other embodiments. For example, in embodiments wherein the needle safety cover 100 is to be reusable, the housing assembly 110 preferably comprises a metallic material, thus allowing the housing assembly 110 to withstand sterilization processes.

The syringe barrel adapter 130 is configured to mount to a standard syringe barrel fitting, such as a Luer or a Luer lock, such that the hollow needle 120 is in fluid connection with a standard syringe barrel (not shown). This arrangement allows fluids to be delivered from the syringe barrel through the hollow needle to the patient (such as during an injection), or allows fluids to be withdrawn from the patient through the hollow needle to the syringe barrel (such as when taking a blood sample). As illustrated in FIGS. 2 and 3, the syringe barrel adapter 130 can be mounted onto the housing assembly 110 using a threading mechanism, a snap fit mechanism, or any other appropriate attachment mechanism, such as with an adhesive. In a modified embodiment, the syringe barrel adapter 130 can be made integral with the housing assembly 110 by molding these two components into a single piece.

In a preferred embodiment, the syringe barrel adapter 130 is freely rotatable with respect to the housing assembly 110, thus allowing the user to rotate the syringe barrel as required for convenience. For example, if the syringe barrel has volumetric markings, the user may wish to continuously monitor the volume of fluid injected to, or withdrawn from, the patient, thus making it convenient to rotate such volumetric markings toward the user. The syringe barrel adapter 130 preferably comprises a polymeric material, although other appropriate materials can be used in other embodiments. For example, in embodiments wherein the needle safety cover 100 is to be reusable, the syringe barrel adapter 130 preferably comprises a metallic material, thus allowing the syringe barrel adapter 130 to withstand sterilization processes.

As illustrated in FIG. 3, the syringe barrel adapter 130 comprises an axial feed tube 132 which is in fluid connection with the hollow needle 120. The hollow needle 120 is preferably fixedly secured to the syringe barrel adapter 130 with an epoxy, thus allowing the hollow needle 120 to be rotated by rotating the syringe barrel adapter 130. Such an arrangement advantageously allows the user to rotate the hollow needle 120 to a desired orientation, as desired in embodiments wherein the hollow needle comprises a beveled tip 122, such as illustrated in FIG. 1. As described above, this arrangement provides for fluid connection between a syringe barrel mounted to the syringe barrel adapter 130 and the patient's body via the axial feed tube 132 and the hollow needle 120. In other embodiments, the hollow needle 120 is rotatable with respect to the syringe barrel adapter 130. Such embodiments allow the user to rotate the syringe barrel adapter 130 as required for convenience, without simultaneously rotating the hollow needle 120. In particular, rotation of the hollow needle 120 while the hollow needle 120 is positioned within a patient's vasculature presents the risk of injuring the patient with the rotating beveled tip 122.

Referring now to FIGS. 2 and 3, the housing assembly 110 preferably further comprises a conduit 142 positioned askew with respect to an axis defined by the hollow needle 120 and the axial feed tube 132. The conduit 142 is configured to movably receive an elongate protective sheath 140, such that the elongate protective sheath 140 is movable between an armed position (illustrated in FIGS. 1 through 3) and a deployed position (illustrated in FIG. 4). As illustrated in FIG. 2, the protective sheath 140 preferably further comprises an elongate slit 148, thus allowing the hollow needle 120 to pass from outside the protective sheath 140 to inside the protective sheath 140.

Figure 4:
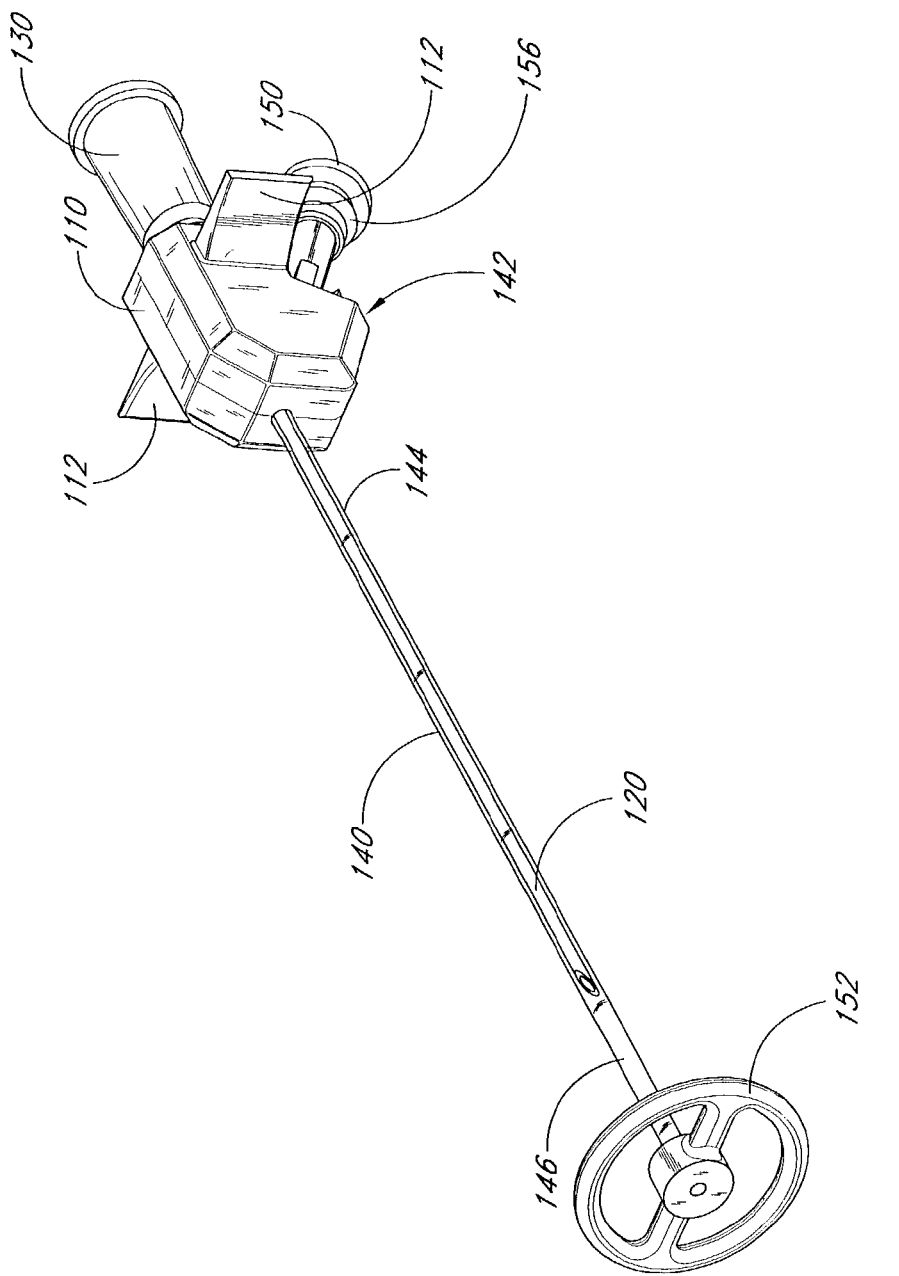
FIG. 4 is a is a perspective view of a needle safety cover in a post-use, or "deployed", configuration.

The elongate protective sheath has a proximal portion 144 and a distal portion 146 opposite the proximal portion 144. The protective sheath distal portion 146 is preferably positioned over the hollow needle 120 when the protective sheath 140 is in the armed position, as illustrated in FIGS. 1 and 2. When the protective sheath 140 is moved into the deployed position, both the protective sheath proximal portion 144 and the protective sheath distal portion 146 are preferably positioned over the hollow needle 120, as illustrated in FIG. 4. In one preferred embodiment, the hollow needle 120 is completely covered by the protective sheath 140 when the protective sheath 140 is moved to the deployed position. That is, in such embodiments the protective sheath 140 has a length that is greater than the length of the hollow needle 120. As described above, the presence of elongate slit 148 allows the protective sheath 140 to freely move between the armed position and the deployed position without requiring movement or reorientation of the hollow needle 120.

In a preferred embodiment, the protective sheath 140 comprises a flexible polymeric material, although other appropriate flexible materials can be used in other embodiments. Specifically, the protective sheath 140 preferably has sufficient flexibility to pass through the conduit and wrap around the hollow needle. In addition, the protective sheath 140 preferably has sufficient elastic characteristics such that the slit 148 is biased in a closed position, thus preventing the hollow needle 120 from leaving the protective sheath 140 when the protective sheath 140 is in the deployed position. Providing the protective sheath 140 with an increased flexibility further allows the user to easily move the protective sheath 140 into a convenient position (for example, held close to the housing assembly 110).

Referring again to FIG. 1, in certain embodiments of the needle safety cover 100, the elongate protective sheath 140 preferably further comprises a proximal finger press 150 and a distal manipulation ring 152 configured to assist the user in moving the protective sheath 140 between the armed position and the deployed position. In particular, in one preferred method of use, the user can deploy the protective sheath 140 by pushing on the proximal finger press 150 with one hand while holding the housing assembly 110 stationary with the other hand. In another preferred method of use the user can deploy the protective sheath 140 by pulling on the housing assembly finger grips 112 with one hand while holding the distal manipulation ring 152 or the proximal finger press 150 stationary with the other hand. One of ordinary skill in the art will recognize that other methods of deploying the protective sheath 140 are equivalent.

Preferably, before use, the needle safety cover 100 is prepared (that is, manufactured) in the armed position (illustrated in FIG. 1) with the hollow needle 120 exposed. Preferably, static friction between the protective sheath 140 and the housing assembly 110 in the conduit 142 prevents the protective sheath 140 from freely sliding through the conduit before or after use. A syringe barrel is first mounted to the syringe barrel adapter 130. If a fluid is to be delivered to the patient, the syringe barrel preferably contains such fluid to be delivered; otherwise if fluid is to be withdrawn from the patient, an empty syringe barrel is mounted to the syringe barrel adapter 130. The hollow needle 120 is then inserted through the patient's skin, and fluid is delivered to, or withdrawn from, the patient as appropriate. When the hollow needle 120 is positioned at the desired location within the patient's body, the protective sheath 140 can be moved from the armed position such that the distal manipulation ring 152 is adjacent to the patient's skin at the injection site. If the syringe barrel contains volumetric markings, the user can monitor the volume of fluid delivered to, or withdrawn from, the patient by carefully rotating the volumetric markings to be easily visible, making sure not to injure the patient's vasculature with the beveled tip 122.

When the hollow needle 120 is ready to be withdrawn from the patient, the protective sheath 140 is moved to the deployed position simultaneously with the removal of the hollow needle 120. Specifically, the user can completely deploy the protective sheath 140 by pushing on the proximal finger press 150 with one hand while holding the housing assembly 110 stationary with the other hand, thus causing the distal manipulation ring 152 to push the patient's body away from the hollow needle 120, which is drawn into the protective sheath 140. In another preferred method of use, the user can completely deploy the protective sheath 140 by pulling on the housing assembly finger grips 112 with one hand while holding the distal manipulation ring 152 against the patient's body with the other hand, thus causing the hollow needle 120 to be drawn into the protective sheath 140. Regardless of how the user holds the housing assembly 110 and the distal manipulation ring 152, the protective sheath 140 is moved to the deployed position by moving the protective sheath 140 relative to the housing assembly 110.

Regardless of the particular method of withdrawing the hollow needle 120 from the patient's body, the protective sheath 140 can be slid over the withdrawn hollow needle 120 simultaneously with the withdrawal of the hollow needle 120 from the patient's body. The elongate slit 148 formed in the protective sheath 140 allows such movement. This configuration advantageously reduces or eliminates the amount of time the withdrawn hollow needle 120 is exposed, thus reducing or eliminating the likelihood of injury or contamination between used needles and other objects and/or people. Furthermore, under this configuration, the portion of the hollow needle 120 withdrawn from the patient's body never passes through the slit 148, thus reducing the likelihood of the slit 148 becoming contaminated with biological fluids. This design advantageously allows biological fluids to be contained within the protective sheath 140.

Preferably, the protective sheath 140 is configured such that it cannot be moved from the deployed position, thus preventing the contaminated hollow needle 120 from becoming exposed after use. For example, in certain embodiments, as illustrated in FIGS. 1 and 2, the conduit 142 portion of the housing assembly 110 further comprises at least one latch 116, such that when the protective sheath 140 is moved to a completely deployed position, an elevated ring 156 on the proximal finger press 150 snaps into the latch 116 and cannot be removed therefrom. The latch 116, although illustrated as integral with the housing assembly 110 in FIG. 2, can also be made integral with the proximal finger press 150. An ordinarily skilled artisan will recognize that a wide variety of conventional latching mechanisms can be used to secure the proximal finger press 150 to the housing assembly 110, thereby securing the protective sheath 140 in the completely deployed position.

In other embodiments, the protective sheath 140 is biased with a curvature, such that when the protective sheath 140 is moved to a completely deployed position, the beveled tip 122 of the hollow needle 120 is offset from the center of the protective sheath 140. In such embodiments, the distal end of the protective sheath 140 (that is, the distal manipulation ring 152) can be provided with a reduced diameter 154, as illustrated in FIG. 3. Because the hollow needle 120 is offset from the center of the protective sheath 140, the presence of the reduced diameter 154 will prevent the hollow needle 120 from later being exposed once completely covered by the protective sheath 140.

Another technique for preventing exposure of the hollow needle 120 after the protective sheath 140 is moved to the deployed position involves mounting a biased pedal 162 within the distal portion 146 of the protective sheath 140, as illustrated in FIG. 3. In such embodiments, the biased pedal 162 is rotatable around a spring-loaded hinge 160, such that when the hollow needle 120 is completely withdrawn into the protective sheath 140, the spring-loaded hinge 160 exerts a force 164 on the pedal 162 which causes the pedal 162 to block the opening in the distal manipulation ring 152, and prevents the hollow needle 120 from leaving the protective sheath 140.

Figure 5:
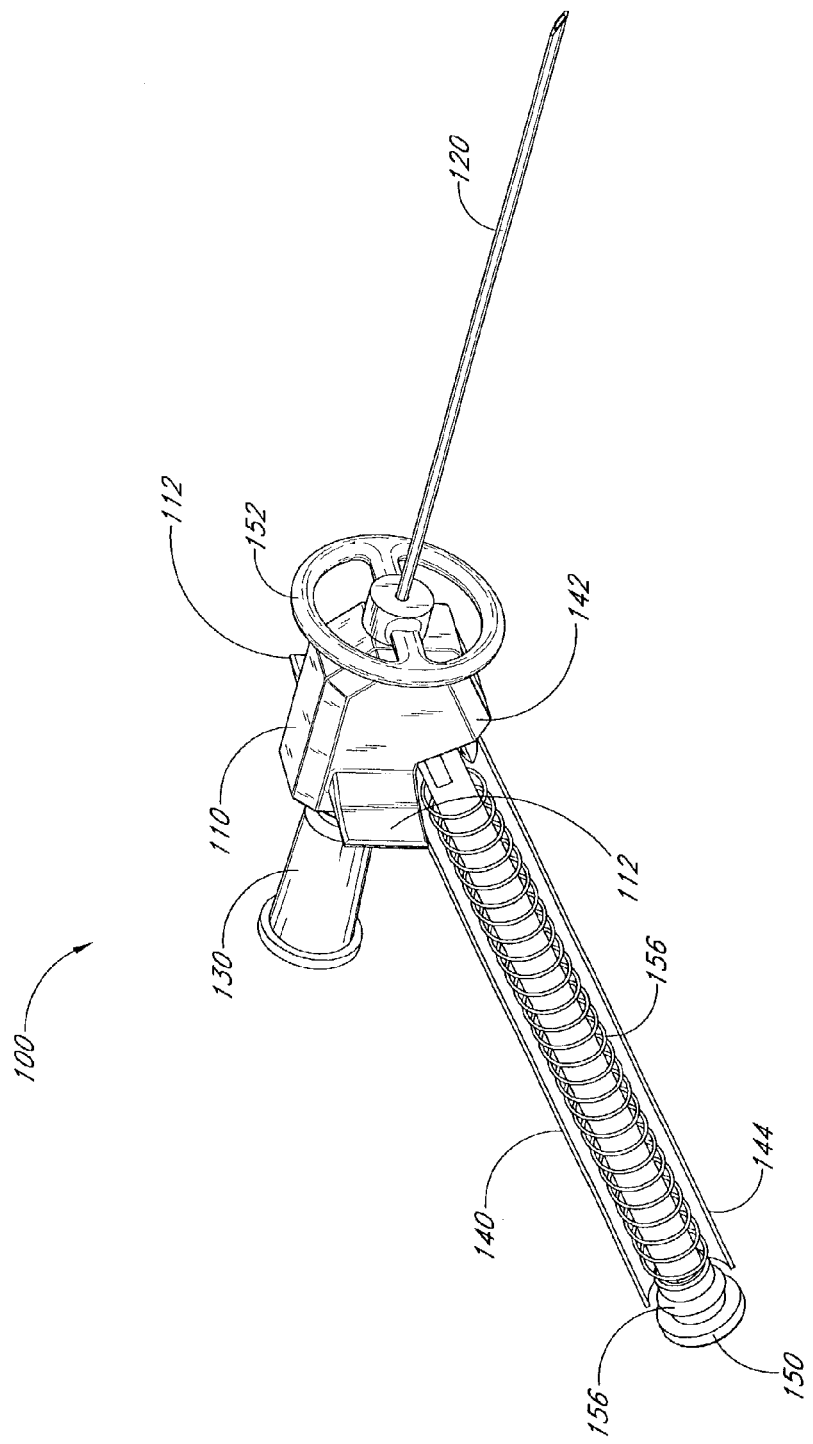
FIG. 5 is a perspective view of a modified needle safety cover having a spring loaded safety sheath.

In a modified embodiment, illustrated in FIG. 5, the protective sheath 140 further comprises a spring 156 positioned between the housing assembly 110 and the proximal finger press 150. The spring 156 can be deployed either internally or externally with respect to the protective sheath 140. The spring 156 is held in tension when the protective sheath 140 is in the armed position. Thus, when the clinician wishes to remove the hollow needle 120 from the patient, the spring 156 can be released, thus causing the proximal finger press 150 to be drawn toward the housing assembly 110, and in turn causing the distal manipulation ring 152 to press against the patient's body during withdrawal of the hollow needle 120. The presence of a steady force of the distal manipulation ring 152 against the patient's body during needle withdrawal reduces or eliminates any exposure of the contaminated needle. One of ordinary skill in the art will recognize that a variety of conventional mechanisms for releasing a spring held in tension, such as a button-activated release latch, can easily be adapted for use with the protective sheath 140 as described herein.

As described above, the various embodiments of the needle safety cover 100 described herein provide several advantages. For example, the movement of the protective sheath 140 over the hollow needle 120 during needle withdrawal reduces or eliminates the likelihood of contamination between used needles and other objects and/or people. In particular, the needle safety systems described herein minimize handling of a needle after removal from the patient's body. Additionally, such systems are easy to use, are inexpensive to manufacture, and do not require specialized disposal apparatuses. In particular, because the protective sheath is integral with the needle itself, the various embodiments described herein eliminate the need for separate disposal structures or apparatus.

SCOPE OF THE INVENTION

The above presents a description of a preferred embodiment of a needle safety cover, and of the manner and process of making and using it, in sufficient detail as to enable a person of ordinary skill in the relevant art to make and use the needle safety cover. The needle safety cover described herein is, however, susceptible to modifications and alternate constructions that are fully equivalent. Consequently, the present invention is not limited to the particular embodiments disclosed. On the contrary, the present intention covers all modifications and alternate constructions within the scope of the following claims.

We claim:

1. A needle safety apparatus comprising:
   a hollow needle having a sharpened distal end and a proximal end, the proximal end anchored in a syringe barrel adapter;
   a protective sheath having a proximal region, a distal region and a slit running between the proximal region and the distal region, the protective sheath movable between an armed position and a deployed position, wherein when the protective sheath is in the armed position the hollow needle passes through the slit in the protective sheath distal region, and when the protective sheath is in the deployed position the hollow needle passes through the slit in the protective sheath proximal region; and
   a spring that is mechanically coupled to the protective sheath, the spring biasing the protective sheath in the deployed position.

2. The needle safety apparatus of claim 1, further comprising a housing assembly supporting the hollow needle and the syringe barrel adapter, the housing assembly having a conduit through which the protective sheath is movably positioned.

3. The needle safety apparatus of claim 2, wherein the housing assembly further comprises a latch configured to prevent further movement of the protective sheath once the protective sheath is in the deployed position.

4. The needle safety apparatus of claim 2, wherein the protective sheath further comprises a latch configured to prevent further movement of the protective sheath relative to the housing assembly once the protective sheath is in the deployed position.

5. The needle safety apparatus of claim 2, wherein the syringe barrel adapter is rotatable with respect to the housing assembly.

6. The needle safety apparatus of claim 1, wherein the protective sheath covers the hollow needle when the protective sheath is in the deployed position.

7. The needle safety apparatus of claim 6, wherein the protective sheath has a reduced diameter in the protective sheath distal region, the reduced diameter configured to prevent the hollow needle from becoming uncovered once the protective sheath is in the deployed position.

8. The needle safety apparatus of claim 1, further comprising a distal manipulation ring surrounding the distal region of the protective sheath.

9. The needle safety apparatus of claim 8, wherein the distal manipulation ring has an inner diameter smaller than an inner diameter of the protective sheath.

10. An apparatus comprising:
    a hollow needle configured for insertion into a patient's body;
    a syringe barrel adapter in fluid communication with the hollow needle;
    a housing assembly supporting the hollow needle and the syringe barrel, the housing assembly having a conduit through which an elongate protective sheath is movably disposed, the elongate protective sheath movable within the conduit between an armed position wherein a portion of the hollow needle is exposed, and a deployed position wherein the hollow needle is covered by the protective sheath; and
    a spring that is positioned within the elongate protective sheath, the spring biasing the elongate protective sheath in the deployed position.

11. The apparatus of claim 10, wherein the housing assembly further comprises a latch configured to prevent further movement of the elongate protective sheath once the protective sheath is in the deployed position.

12. The apparatus of claim 10, wherein the syringe barrel adapter is rotatable with respect to the housing assembly.

13. The apparatus of claim 10, wherein an axial slit is formed along the elongate protective sheath, the slit configured to allow the hollow needle to pass through the axial slit.

14. The apparatus of claim 10, wherein the protective sheath has a reduced diameter in a protective sheath distal region, the reduced diameter configured to prevent the hollow needle from becoming uncovered once the protective sheath is in the deployed position.

15. A method comprising:
    inserting an elongate hollow needle into a patient's body, the elongate needle anchored in a housing assembly having a conduit through which an elongate protective sheath is movably disposed;
    positioning a distal portion of the elongate protective sheath adjacent to the patient's body;
    withdrawing the elongate hollow needle from the patient's body while substantially maintaining the distal portion of the elongate protective sheath in a position adjacent to the patient's body; and
    releasing a spring to substantially maintain the distal portion of the elongate protective sheath in a position adjacent to the patient's body.

16. The method of claim 15, further comprising covering the elongate hollow needle with the protective sheath.

17. The method of claim 16, further comprising securing the elongate protective sheath to the housing assembly once the elongate hollow needle is covered, thus preventing movement of the elongate protective sheath with respect to the housing assembly.

18. The method of claim 15, wherein the elongated hollow needle is passed through an axial slit formed in the elongate protective sheath.

* * * * *